United States Patent [19]
King et al.

[11] Patent Number: 5,731,151
[45] Date of Patent: Mar. 24, 1998

[54] REGULATOR OF CONTACT-MEDIATED HEMOLYSIN

[75] Inventors: C. Harold King, Rex; Thomas M. Shinnick, Atlanta, both of Ga.; Mundayoor Sathish, Bombay, India

[73] Assignee: The United States of America as represented by the Secretary of the Department of Health and Human Services, Washington, D.C.

[21] Appl. No.: 557,115

[22] PCT Filed: May 24, 1994

[86] PCT No.: PCT/US94/05869

§ 371 Date: Jun. 26, 1996

§ 102(e) Date: Jun. 26, 1996

[87] PCT Pub. No.: WO94/28137

PCT Pub. Date: Dec. 8, 1994

[51] Int. Cl.⁶ .................. C12Q 1/68; C12N 15/00; C12P 1/00; C12P 21/06
[52] U.S. Cl. .................. 435/6; 435/41; 435/69.1; 435/71.1; 435/91; 536/25.3
[58] Field of Search .................. 435/6, 41, 69.1, 435/71.1, 91; 536/25.3

[56] References Cited

PUBLICATIONS

Kitagawa et al. "Structural analyses of the umu operon required for inducible mutagenesis in *Escherichia coli*." PNASUSA 82:4336–4340 1985.

C. Harold King et al., "Cloning and Expression of a Contact Hemolysin from *Mycobacterium tuberculosis*", Abstract, 1992 American Soc. for Microbiology General Meeting, May 1992.

Pascale Cossart et al., "Listeriolysin O is Essential for Virulence of *Listeria monocylogenes*: Direct Evidence Obtained by Gene Complementation." *Infection and Immunity*, 57(11):3629–3636 (Nov. 1989).

M. Kuhn et al., "Hemolysin Supports Survival But Not Entry of the Intracellular Bacterium *Listeria monocytogenes*," *Infection and Immunity*, 56(1):79–82 (Jan. 1988).

Philippe J. Sansonetti et al., "Multiplication of *Shigella flexneri* within HeLa Cells:Lysis of the Phagocytic Vacuole and Plasmid–Mediated Contact Hemolysis." *Infection and Immunity*, 51(2):461–469 (Feb. 1986).

Eva S.Leake et al. "Phagosomal Membranes of *Mycobacterium bovis* BCG–Immune Alveolar Macrophages are Resistant to Disruption by *Mycobacterium tuberculosis* H37Rv." *Infection and Immunicy* 45(2):443–446 (Aug. 1984).

Quentin N. Myrvik et al., "Disruption of Phagosomal Membranes of Normal Alveolar Macrophages by the H37Rv Strain of *Mycobacterium tuberculosis*," *Am. Rev. Respir. Dis.* 129:322–328 (1984).

Rodney A. Welch et al., "Characterization of *Escherichia coli* Hemolysins Conferring Quantitative Differences in Virulence." *Infection and Immunity* 43(1):156–160 (1984).

*Primary Examiner*—James C. Housel
*Assistant Examiner*—Rodney P. Swartz
*Attorney, Agent, or Firm*—Jones & Askew, LLP

[57] ABSTRACT

The present invention relates to a nucleic acid that encodes a hemolysin protein and to a nucleic acid that encodes a positive regulator of hemolysis. The nucleic acid can be the basis of a vaccine against tuberculosis. The nucleic acid can be inserted into an avirulent vaccine strain such as *M. bovis* BCG.

15 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 1023 base pairs (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: E. coli (vii) IMMEDIATE SOURCE:
        (B) CLONE: pTBLA3

(ix) FEATURE:
        (A) NAME/KEY: misc_feature
        (B) LOCATION: 679..682
        (D) OTHER INFORMATION: /note= "/product=Translation start
            codon for umuD coding sequences"

(xi) SEQUENCE DESCRIPTION: SEQ ID NO:1:

| | | | | | |
|---|---|---|---|---|---|
| GTCGACATCA | CCCGATTGAT | CATGTTGCGT | GAAGCTCATA | ATTGCTGCTA | AAGCAAACCA | 60 |
| CGCCACAGCG | ACGAAACAGA | TCTTTTTGTT | TGAACCAGGG | ATCGCCCATT | TTAACGCCAA | 120 |
| GCGCCTTTGC | CTCAGTGTTT | CGGGCGATAA | CGCAACCGTC | ATTATTCGAT | AGCACAACCA | 180 |
| CCGGTTTACC | CCATAAATCA | GGGCGAAACA | CCGTCTCACA | GCTGGCATAA | AACGCGTTTA | 240 |
| CATCACAGAG | GGCAAACATC | AGCGCATCGC | CTTAAGACGT | GGTTCACCAC | ACCAAAAGAC | 300 |
| ATCCAGCGTA | TCTTCACTAC | TGATGGGTAA | TGGGCGGAGT | ACGCGCTGTT | CATGGGAATA | 360 |
| AGCTGTACCG | TCGGGCGTAG | TTGCAATTTT | TTCACCGTAA | ACTCGCCGTC | AACAGCAGCG | 420 |
| ATGACAATAT | CACCATGGCT | GGCGGTAATA | GCGCTATCGA | CAATCAGTAA | ATCACCGTCA | 480 |
| CTAATTCCAC | CATCAATCAT | AGAATCACCA | CTTGCTTTGA | CGAAGTAAGT | CGCGCTGGGA | 540 |
| TGCTGGATCA | ACAGTTGATT | CAGATCGATG | CGCTGTTCAA | CGTAATCTGC | TGCCGGTGAA | 600 |
| GGAAAGACCA | CACTGAACAA | GATCGCTTAA | ATAGCGGAAA | AGTCACAATT | TCGCGGAGAT | 660 |
| CCGCAGGCTT | GATAAACAAC | ATAATAATCT | GCCTGAAGTT | ATACTGTTTT | TATATACAGT | 720 |
| AGTCTGTTCT | TGCCAGCAGA | TCAATACTGA | TTCAGGCTAT | CAATATTTGT | CGCTGCATAG | 780 |
| GCTGCTGATT | TTTCGTTCTC | TTATCTTGTG | CTCACGTGGC | CTTCTGGCGA | CGACGCTCAT | 840 |
| CCAGCAGAAA | TGAAAAATAT | CACCCGGCTA | AAAAATAGAA | TAGAAGCATC | GCCATAATGA | 900 |
| CATTAAACAT | TGTTTGGATA | TTTATCATAT | TTAATAGAAA | TAAAGACATT | GACGCATCCC | 960 |
| CGCCCGGCTT | AACTATGAAT | TAGATGAAGT | AAAATTTATT | AATAGTTGTA | AAACAGGAGT | 1020 |
| TTC | | | | | | 1023 |

(2) INFORMATION FOR SEQ ID NO:2:

(i) SEQUENCE CHARACTERISTICS:
        (A) LENGTH: 1020 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: E. coli (ix) FEATURE:
        (A) NAME/KEY: misc_feature -continued ( B ) LOCATION: 99..101
        ( D ) OTHER INFORMATION: /note= "Translation start codon"

( i x ) FEATURE:
        ( A ) NAME/KEY: misc_feature
        ( B ) LOCATION: 76..81
        ( D ) OTHER INFORMATION: /note= "5/6 match with -10
            consensus sequence for E. coli promoters (TATAAT)"

( i x ) FEATURE:
        ( A ) NAME/KEY: misc_feature
        ( B ) LOCATION: 47..52
        ( D ) OTHER INFORMATION: /note= "4/6 match with -35
            consensus sequence (TTGACA)"

( i x ) FEATURE:
        ( A ) NAME/KEY: misc_feature
        ( B ) LOCATION: 87..94
        ( D ) OTHER INFORMATION: /note= "4/8 match with the E. coli
            consensus sequence for ribosome binding sites (AGGAAAGG)"

( x i ) SEQUENCE DESCRIPTION: SEQ ID NO:2:

| | | | | | |
|---|---|---|---|---|---|
| CCCGCCCGGC | TAACTATGAA | TTAGATGAAG | TAAAATTTAT | TAATAGTTGT | AAAACAGGAG | 60 |
| TTTCATTACA | ATTTATATAT | TTAAAGAGGC | GAATGATTAT | GACTGAAATC | GTTGCAGATA | 120 |
| AAACGGTAGA | AGTAGTTAAA | AACGCAATCG | AAACCGCAGA | TGGAGCATTA | GATCTTTATA | 180 |
| ATAAATATCT | CGATCAGGTC | ATCCCCTGGC | AGACCTTTGA | TGAAACCATA | AAAGAGTTAA | 240 |
| GTCGCTTTAA | ACAGGAGTAT | TCACAGGCAG | CCTCCGTTTT | AGTCGGCGAT | ATTAAAACCT | 300 |
| TACTTATGGA | TAGCCAGGAT | AAGTATTTTG | AAGCAACCCA | AACAGTGTAT | GAATGGTGTG | 360 |
| GTGTTGCGAC | GCAATTGCTC | GCAGCGTATA | TTTGCTATT | TGATGAGTAC | AATGAGAAGA | 420 |
| AAGCATCCGC | CCAGAAAGAC | ATTCTCATTA | AGGTACTGGA | TGACGGCATC | ACGAAGCTGA | 480 |
| ATGAAGCGCA | AAAATCCCTG | CTGGTAAGCT | CACAAAGTTT | CAACAACGCT | TCCGGGAAAC | 540 |
| TGCTGGCGTT | AGATAGCCAG | TTAACCAATG | ATTTTTCAGA | AAAAAGCAGC | TATTTCCAGT | 600 |
| CACAGGTAGA | TAAAATCAGG | AAGGAAGCAT | ATGCCGGTGC | CGCAGCCGGT | GTCGTCGCCG | 660 |
| GTCCATTTGG | ATTAATCATT | TCCTATTCTA | TTGCTGCGGG | CGTAGTTGAA | GGAAAACTGA | 720 |
| TTCCAGAATT | GAAGAACAAG | TTAAATCTG | TGCAGAATTT | CTTTACCACC | CTGTCTAACA | 780 |
| CGGTTAAACA | AGCGAATAAA | GATATCGATG | CCGCCAAATT | GAAATTAACC | ACGAAATAG | 840 |
| CCGCCATCGG | TGAGATAAAA | ACGGAAACTG | AAACAACCAG | ATTCTACGTT | GATTATGATG | 900 |
| ATTTAATGCT | TTCTTTGCTA | AAAGAAGCGG | CCAAAAAAAT | GATTAACACC | TGTAATGAGT | 960 |
| ATCAGAAAAG | ACACGGTAAA | AAGACACTCT | TGAGGTACC | GAGCTCGAAT | TCCCCGGATG | 1020 |

( 2 ) INFORMATION FOR SEQ ID NO:3:

( i ) SEQUENCE CHARACTERISTICS:
        ( A ) LENGTH: 309 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

```
Met Thr Glu Ile Val Ala Asp Lys Thr Val Glu Val Val Lys Asn Ala
 1               5                  10                  15
Ile Glu Thr Ala Asp Gly Ala Leu Asp Leu Tyr Asn Lys Tyr Leu Asp
                20                  25                  30
```

| | | | | | | | | | | | | | | | |
|---|---|---|---|---|---|---|---|---|---|---|---|---|---|---|---|
| Gln | Val | Ile 35 | Pro | Trp | Gln | Thr | Phe 40 | Asp | Glu | Thr | Ile | Lys 45 | Glu | Leu | Ser |
| Arg | Phe 50 | Lys | Gln | Glu | Tyr | Ser 55 | Gln | Ala | Ala | Ser | Val 60 | Leu | Val | Gly | Asp |
| Ile 65 | Lys | Thr | Leu | Leu | Met 70 | Asp | Ser | Gln | Asp | Lys 75 | Tyr | Phe | Glu | Ala | Thr 80 |
| Gln | Thr | Val | Tyr | Glu 85 | Trp | Cys | Gly | Val | Ala 90 | Thr | Gln | Leu | Leu | Ala 95 | Ala |
| Tyr | Ile | Leu | Leu 100 | Phe | Asp | Glu | Tyr | Asn 105 | Glu | Lys | Lys | Ala | Ser 110 | Ala | Gln |
| Lys | Asp | Ile 115 | Leu | Ile | Lys | Val | Leu 120 | Asp | Asp | Gly | Ile | Thr 125 | Lys | Leu | Asn |
| Glu | Ala 130 | Gln | Lys | Ser | Leu | Leu 135 | Val | Ser | Ser | Gln | Ser 140 | Phe | Asn | Asn | Ala |
| Ser 145 | Gly | Lys | Leu | Leu | Ala 150 | Leu | Asp | Ser | Gln | Leu 155 | Thr | Asn | Asp | Phe | Ser 160 |
| Glu | Lys | Ser | Ser | Tyr 165 | Phe | Gln | Ser | Gln | Val 170 | Asp | Lys | Ile | Arg | Lys 175 | Glu |
| Ala | Tyr | Ala | Gly 180 | Ala | Ala | Ala | Gly | Val 185 | Val | Ala | Gly | Pro | Phe 190 | Gly | Leu |
| Ile | Ile | Ser 195 | Tyr | Ser | Ile | Ala | Ala 200 | Gly | Val | Val | Glu | Gly 205 | Lys | Leu | Ile |
| Pro | Glu 210 | Leu | Lys | Asn | Lys | Leu 215 | Lys | Ser | Val | Gln | Asn 220 | Phe | Phe | Thr | Thr |
| Leu 225 | Ser | Asn | Thr | Val | Lys 230 | Gln | Ala | Asn | Lys | Asp 235 | Ile | Asp | Ala | Ala | Lys 240 |
| Leu | Lys | Leu | Thr | Thr 245 | Glu | Ile | Ala | Ala | Ile 250 | Gly | Glu | Ile | Lys | Thr 255 | Glu |
| Thr | Glu | Thr | Thr 260 | Arg | Phe | Tyr | Val | Asp 265 | Tyr | Asp | Asp | Leu | Met 270 | Leu | Ser |
| Leu | Leu | Lys 275 | Glu | Ala | Ala | Lys | Lys 280 | Met | Ile | Asn | Thr | Cys 285 | Asn | Glu | Tyr |
| Gln | Lys 290 | Arg | His | Gly | Lys | Lys 295 | Thr | Leu | Phe | Glu | Val 300 | Pro | Ser | Ser | Asn |
| Ser 305 | Pro | Asp | Ala | Ala | | | | | | | | | | | |

REGULATOR OF CONTACT-MEDIATED HEMOLYSIN

BACKGROUND OF THE INVENTION

1. Field of the Invention

The present invention relates to a nucleic acid that encodes a hemolysin protein and to a nucleic acid that encodes a positive regulator of hemolysis.

2. Background Art

The World Health Organization estimates that more than 2 billion persons worldwide are or have been infected with *Mycobacterium tuberculosis*, and tuberculosis causes more than 3.5 million deaths annually (1). The human immunodeficiency virus (HIV) epidemic has complicated the epidemiology of tuberculosis (2), and much of the recent increase in tuberculosis in developed countries can be traced to the enhanced susceptibility of AIDS patients to developing this disease (3).

*M. tuberculosis* is an intracellular pathogen which multiplies within cells of the host's immune system, primarily macrophages (4). Uptake of the bacillus by macrophages is thought to be mediated by complement component C3 and complement receptor (5). After entering the cell, *M. tuberculosis* inhibits phagosome-lysosome fusion (6,7) and the acidification of the phagosome (8). *M. tuberculosis* then multiplies within the unfused vacuole (9). Macrophages heavily ladened with bacilli ultimately lyse and release the bacilli.

Studies of other bacterial pathogens have shown that soluble and membrane-bound cytolysins are important virulence factors. For example, strains of *Escherichia coli* expressing alpha-hemolysin are 10- to 1000-fold more virulent in animal models than strains lacking alpha-hemolysin (10). Similarly, strains of *Bordetella pertussis* lacking adenylate cyclase/hemolysin display reduced virulence in mouse models (11), and this phenotype can be reversed by trans-complementation with a plasmid expressing the adenylate cyclase/hemolysin (12).

Cytolysins also play important roles in the ability of intracellular bacterial pathogens to enter, replicate within, and exit host cells (13,14,15). The soluble cytolysin of *Listera monocytogenes*, listeriolysin O, is required for the intracellular growth of this organism in macrophages (16, 17,18). Expression of listeriolysin O in *Bacillus subtilis* allows this non-pathogen to escape from the phagosome and multiply within macrophages (19). A membrane-bound cytolysin has also been implicated in the escape from phagosomes and intracellular growth of *Shigella flexneri* (20), and more recently the Shigella cytolysin, but not the Listeria cytolysin, has been shown to induce macrophage cell death through apoptosis (21).

Hemolytic activity in *M. tuberculosis*, however, has not been studied, due in part to unique difficulties in culturing these cells. In particular, these organisms release organic molecules which remain in the culture medium and cause dumping of the cells, a phenomenon known to scientists in the field. Thus, hemolysis assays would be a practically difficult problem with this organism. Furthermore, there has been no correlation in the literature between hemolysins and virulence of *M. tuberculosis*.

The present invention is based in part upon the vital and unexpected discovery that virulent strains of *M. tuberculosis* possess hemolytic activity while avirulent strains do not. Such a discovery will help provide long-awaited understanding of the mechanisms of infection by this organism and crucial means of treating and preventing infection and death from *M. tuberculosis*.

The present invention is also based upon the discovery of an *E. coli* gene that regulates hemolysis when placed in any of several different bacterial organisms. This gene therefore, can be utilized to provide greatly improved vaccine strains against *M. tuberculosis* as it can aid these vaccines in causing cell-mediated immunity. Such vaccines are greatly needed in light of the large numbers of people infected with *M. tuberculosis* and the devastating effects of infection. Current vaccines, such as the strain *M. bovis* BCG, have met with only limited success, since, over time after vaccination, protection against tuberculosis declines.

SUMMARY OF THE INVENTION

The present invention provides an isolated double-stranded nucleic acid comprising the sequence set forth in SEQ ID NO:2. This sequence is an *E. coli*-derived hemolysin regulator. The present invention also provides the protein encoded by the above nucleic acid, or a biologically active portion thereof.

The present invention also provides a vaccine comprising a host containing a vector which includes an isolated double-stranded nucleic acid comprising the sequence set forth in SEQ ID NO:2.

Also provided by the instant invention is a method of promoting an immune response in a subject against *Mycobacterium tuberculosis* comprising administering to the subject a suitable host, such as *M. bovis* BCG or *M. smegmatis*, containing a vector which includes an isolated double-stranded nucleic acid comprising the coding sequences set forth in SEQ ID NO:2.

The present invention further provides a method of enhancing the immunogenic effects in a subject of an *M. bovis* BCG vaccine comprising inserting a vector which includes an isolated double-stranded nucleic acid comprising the coding sequences set forth in SEQ ID NO:2 into the *M. bovis* BCG vaccine prior to administering the vaccine to the subject.

The present invention also provides a double-stranded nucleic acid positively regulated by the protein comprising the polypeptide encoded by SEQ ID NO:2, wherein the nucleic acid encodes a protein having hemolysis activity.

Also provided is a method of detecting the presence of a virulent strain of *Mycobacterium tuberculosis* in a sample comprising (a) identifying the presence of a *Mycobacterium tuberculosis* nucleic acid sequence in the sample; and (b) detecting contact-mediated hemolytic activity in the sample, the presence of *Mycobacterium tuberculosis* and contact mediated hemolytic activity indicating the presence of a virulent strain of *Mycobacterium tuberculosis*.

DETAILED DESCRIPTION OF THE INVENTION

The present invention may be understood more readily by reference to the following detailed description of specific embodiments and the Examples included therein.

As used herein, "a" or "an" can mean one or more depending on the context in which it is used.

The examples presented herein show that the virulent H37Rv strain of *M. tuberculosis* expresses a cytolytic activity that is significantly increased when the bacteria are in close contact with erythrocytes. A recombinant clone carrying an *E. coli* genomic locus that causes expression of a cytolytic activity when transferred into several organisms such as *M. tuberculosis* and *M. smegmatis* also causes expression of a cytolytic activity that is significantly increased by close contact with erythrocytes.

The findings provided herein indicate that *M. tuberculosis* expresses a contact-dependent cytolysin that is either not expressed or expressed below detectable levels in an attenuated strain of *M. tuberculosis* and an attenuated vaccine strain of *M. bovis*. These findings also show that *E. coli* contains a nucleic acid coding sequence that, when transfected into other organisms under the control regulatory sequences compatible with that organism, induces a hemolytic phenotype in these organisms. Therefore, this gene is referred to herein as a regulator of hemolysis.

SEQ ID NO:2 sets forth the sequence of the isolated *E.coli* gene encoding a regulator of hemolysis. This gene encodes a protein found, as described herein, to regulate hemolysis in several bacterial organisms. For example, this sequence, when transfected into *M. tuberculosis, M. smegmatis,* or *E. coli* under appropriate regulatory sequences, causes the organism to demonstrate hemolytic activity. Given this discovery, various therapies can be designed to treat or prevent the hemolysis activity of *M. tuberculosis.*

Provided herein is an isolated double-stranded nucleic acid comprising the nucleic acid sequence set forth in SEQ ID NO:2. Additionally provided is the coding nucleic acid sequence as well as the non-coding, i.e., regulatory region, nucleic acid sequence of this nucleic acid. As noted in the sequence listing in SEQ ID NO:2, the non-coding region of SEQ ID NO:2 includes nucleotides 1–98, and the coding region includes nucleotides 99–1020 or portions thereof. Also provided is the purified polypeptide encoded by the nucleic acid, which amino acid sequence is set forth in SEQ ID NO:3. The invention further provides an isolated nucleic acid encoding this amino acid sequence set forth in SEQ ID NO:3. The nucleic acid can, if desired, include regulatory sequences operably linked to the coding sequence to control expression of this gene, such that the protein can be expressed, for example, by a host which carries the gene.

By "isolated" is meant separated from other nucleic acids found in the source organism. The nucleic acid of SEQ ID NO:2 is genomic sequence and thus includes at least some of the regulatory sequences utilized; however, any other regulatory regions can be operably linked to the coding sequences for proper expression of the gene in a selected organism. "Operably linked" means the sequences are attached such that the regulatory regions can direct the expression of the coding region. Therefore, other regulatory regions can be substituted in place of the *E. coli* regulatory region. For example, the *E. coli* promoter can be replaced by an *M. tuberculosis* promoter, such as the known heatshock hsp60 promoter. Such additional useful regulatory regions are known or can be found with techniques standard in the art. (Sambrook et al., *Molecular Cloning: A Laboratory Manual,* 2nd Ed., Cold Spring Harbor Laboratory, Cold Spring Harbor, N.Y. (1989)).

Additionally provided herein is the noncoding region of the nucleic acid of SEQ ID NO:2 operably linked to a reporter gene. Such reporter genes are well known in the art, as are the methods for performing the linkage Examples of such reporter genes include the β-gal gene, LacZ gene and luciferase gene. Such constructs can be useful in screening for compounds that inhibit or increase expression of this gene. Thus, the regulatory region reporter construct can be useful for screening for compounds that bind to the regulatory regions of the gene for the regulation of hemolysis. Such screenings could be readily performed according to standard methods for screening for expression of a selected reporter gene, e.g., for detecting the presence of the reporter gene product.

Also provided herein is a double-stranded nucleic acid encoding a protein having hemolysis activity and positively regulated by the positive regulator of hemolysis described herein. Hemolysis activity can be assayed utilizing the hemolysis assay described herein. By "positively regulated" is meant that the presence of the regulator increases expression of the hemolysin protein's hemolytic activity.

In addition, the invention also provides a nucleic acid encoding a regulator of hemolysin which is homologous to the regulator of hemolysin described herein. Such a homologous nucleic acid sequence can be used for example to simultaneously detect related strains or as a basis for a multiprotective vaccine. For example, Southern blot analysis indicates that a homolog for hemolysin exists at least in *M. smegmatis, M. tuberculosis* H37Ra, *E. coli* and *M. bovis.* However, given the lack of cytolytic activity expressed by these avirulent bacteria in the hemolysis assay of this invention, this hemolysin gene either is not expressed, is expressed at undetectable levels, or is mutated such that its gene product is no longer hemolytic in its activity. Such homologous regulators of hemolysin can be isolated using the procedures set forth herein or by standard procedures utilizing primers and probes derived from the Sequence Listing.

A nucleic acid which selectively hybridizes with the nucleic acid encoding this positive regulator of hemolysis is also contemplated. As used herein, "selectively hybridizes" means that the nucleic acid specifically hybridizes to its target (i.e., complementary) nucleic acid based upon complementarity between the two sequences, rather than random non-specific, non-selective hybridization, under suitable stringent hybridization conditions. In other words, the sequences of the nucleic acid utilized for hybridization are unique to the target sequence such that the target sequence can be detected apart from other nucleic acids under suitable stringent hybridization conditions. Suitably stringent conditions will naturally vary based on the length of the nucleic acids. Thus, a nucleic acid that selectively hybridizes with a nucleic acid of the antigen coding sequence will not selectively hybridize under stringent conditions with a nucleic acid for a different antigen, and vice versa. The invention provides examples of these nucleic acids, so that the degree of complementarity required to distinguish selectively hybridizing from nonselectively hybridizing nucleic acids under stringent conditions can be clearly determined for each nucleic acid.

"Stringent hybridization conditions" refers to the washing conditions used in a hybridization protocol. In general, the washing conditions should be a combination of temperature and salt concentration chosen so that the denaturation temperature is approximately 5°–20° C. below the calculated $T_m$ of the hybrid under study. The temperature and salt conditions are readily determined empirically in preliminary experiments in which samples of reference DNA immobilized on filters are hybridized to the probe or protein coding nucleic acid of interest and then washed under conditions of different stringencies. For example, hybridizations with oligonucleotide probes shorter than 18 nucleotides in length can be done at 5°–10° C. below the estimated $T_m$ in 6X SSPE, then washed at the same temperature in 2X SSPE (see, e.g., Sambrook et al.). The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C.

Additionally, the nucleic acids of the invention can have at least 80% homology with the coding nucleotides of SEQ ID NO:2 that are not subject to the degeneracy of the genetic code, i.e., with the non-"wobble" nucleotides (the wobble nucleotides usually being the third nucleotide in a codon) in the coding sequence. Preferably, the nucleic acids will have 90%, or more preferably, 95%, or even more preferably, 99% homology with the coding nucleotides of SEQ ID NO:2 that are not subject to the degeneracy of the genetic code. The nucleic acids can be at least 18, 50, 100, 150, 200, 300, 500, 750 or 1000 nucleotides in length.

Such a nucleic acid can also comprise a primer or probe, for example, that hybridizes to either strand of the nucleic acid and can be used in amplification procedures or in detection of the organism. Such a nucleic acid can also be used, for example, in inhibitory antisense therapy to bind to mRNA molecules transcribed from the coding DNA strand and prevent translation, and to thereby inhibit hemolysis. In addition, the selectively hybridizing nucleic acid can be the length of the entire coding region and encode a substantially similar protein having the hemolysin activating activity. The sequences of such nucleic acids can be selected based on the genomic nucleotide sequence and the intended use for the particular nucleic acid.

Also provided is a nucleic acid which selectively hybridizes with the double-stranded nucleic acid encoding the hemolysin. Thus, this nucleic acid can selectively hybridize, as defined herein, to either strand of the nucleic acid encoding hemolysin, and can be used for such functions as primers, probes, and antisense binding to mRNA transcribed from the nucleic acid to inhibit hemolytic activity or to detect the presence of *M. tuberculosis*. This nucleic acid from *M. tuberculosis* can be readily ascertained by, for example, amplification of homologous sequences using degenerative primer(s) PCR (Sadaie, Y. et al., *Gene*, 98:101–105 (1991); Scaramuzzi, C. D., *Current Genetics*, 22:421–427 (1992)) and using, for example, another cytolysin sequence.

Any nucleic acid of the present invention in a vector is also provided. Such a vector can include the nucleic acid as well as additional nucleic acid sequences having numerous functions, such as restriction endonuclease sites, sequences allowing replication of the vector, marker genes, and other features, known and standard in the art (see e.g., Sambrook et al.). Typical vectors include numerous plasmids, cosmids and viral constructs. Nucleic acids can be placed into vectors by standard means known in the art. Fragments of nucleic acids can also be placed into vectors, such fragments being generated by known, standard techniques such as recombinant methods and synthesis methods. The vectors of the invention can be in a host, particularly a host capable of expressing the protein.

There are numerous *E. coli* expression vectors known to one of ordinary skill in the art that are useful for the expression of the antigen. Other microbial hosts suitable for expression use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell. In addition, any number of a variety of well-known promoters will be present. The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Provided herein is a vector comprising any herein described nucleic acid in a host. Such a "host" can be any organism capable of maintaining the vector within the organism. The host is preferably one that is suitable for expression of the nucleic acid. Particularly useful hosts are attenuated organisms currently used for vaccine purposes, such as *M. bovis* BCG, bacteria closely related to virulent *M. tuberculosis*, such as *M. smegmatis*, and other bacteria that would maintain copies of the vector such as *E. coli*. The vector can be readily placed in the host by any of several means, depending upon the type of vector used, such as transfection, transformation, electroporation or microinjection, which are standard techniques (see Sambrook et al.)

A particularly useful host is one including a vector in which is inserted a nucleic acid encoding the present regulator of hemolysin. SEQ ID NO:2 provides the genomic sequence of an example nucleic acid encoding this hemolysis regulator which can be inserted into any suitable vector, as described herein and known in the art, for the selected host, by methods standard in the art. However, any selected nucleic acid sequence encoding the regulator protein can be utilized. For example, due to the degeneracy of the genetic code, the coding sequences can be altered. Furthermore, depending upon the host selected, the regulatory sequences can be modified to select regulatory sequences capable of allowing expression of the gene in that specific host. Hosts can be selected as described herein. One particularly useful host can be *M. bovis* BCG, a vaccine strain of mycobacterium. An *M. bovis* BCG host containing the coding nucleic acid sequences under the control of suitable regulatory sequences can be particularly useful for promoting an immune response in a subject. Any selected host and vector can be readily tested for promoting an immune response by standard immune response testing. This host can be in a pharmaceutically acceptable carrier.

Each gene may exist as a single contiguous sequence or may, became of intervening sequences and the like, exist as two or more discontinuous sequences, which are nonetheless transcribed in vivo to ultimately effect the biosynthesis of a protein substantially equivalent to that described above. Such modifications may be deliberate, resulting from, for example, site directed mutations. Such modifications may be neutral, in which case they result in redundant condons specifying the native amino acid sequence or in such modifications which may in fact result in a change in amino add sequence which has either no effect, or only an insignificant effect on activity of the protein. Retention of the activity can be readily monitored by the methods taught herein. Such modifications may include point mutations, deletions or insertions.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "nucleic acid encoding for" a protein may thus refer to one or more genes within a particular individual. Moreover, certain differences in nucleotide sequences may exist between individual organisms, which are called alleles. Such allelic differences may or may not result in differences in amino acid sequence of the encoded polypeptide while still encoding a protein with positive hemolysis regulatory activity or hemolysis activity.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for specific, selective hybridization that distinguishes this gene from other nucleic acids, as described herein (Kunkel et al. *Methods Enzymol.* 154:367 (1987)).

Additionally provided herein is a purified protein comprising the polypeptide whose amino acid sequence is set forth in SEQ ID NO:3, or a biologically active portion thereof. Modifications to the set forth amino acid sequence, such as amino acid substitutions, can be made, as known in the art, as long as the protein retains its biological activity. This protein has the activity of positively regulating hemolysis, which activity can be readily detected by the methods taught therein. By "purified" is meant that the protein is separated from other proteins in the source organism. By "biologically active portion thereof" is meant a fragment of this protein that still retains its biological activity of positively regulating hemolysis, as can readily be determined. Peptide fragments can be made according to routine methods known to those of skill in the art, as elaborated upon below. Additionally, modifications to the amino acids typically occurring in the cell, such as glycosylation and acetylation, can be made.

A protein encoded by a nucleic acid that is positively regulated by the inventive regulator of hemolysin, or a hemolyticly active portion thereof, is also provided herein. This protein has hemolytic activity. The nucleic acid encoding this protein can be positively regulated by the above positive regulator of homolysis, since studies in which the nucleic acid encoding the positive regulator is added to cells that apparently contain an unexpressed hemolysis structural gene and normally demonstrate no hemolysis activity, show that the cells subsequently demonstrate hemolysis activity.

The complete protein as well as any fragment thereof that retains its above-described biological activity is contemplated herein. A "biologically active portion" of any protein herein can also contemplate fragments that retain biological activities such as immunogenicity and immunoreactivity, as can be determined by standard methods known in the art, as elaborated upon below. A "hemolyticly active portion" of a protein retains the function of hemolysis, as can be readily tested by the methods provided herein.

An immunoreactive fragment of any protein provided herein is defined as an amino acid sequence of at least about 5 consecutive amino acids derived from the protein's amino acid sequence. Such fragments can be generated, for example, by mechanical or chemical disruption of the complete protein or, as another example, they can be recombinant proteins obtained by cloning nucleic acids encoding the polypeptide in an expression system capable of producing the protein or fragments thereof. The activity of such fragments can be determined utilizing the methods taught below in the Examples.

The polypeptide fragments of the present invention can also be recombinant peptides obtained by cloning nucleic acids encoding the polypeptide in an expression system capable of producing the antigenic polypeptide or fragments thereof.

The present invention also provides an immunogenic amount of a hemolysin protein of this invention in a pharmaceutically acceptable carrier. An immunogenic amount can be readily determined by standard methods for the specific subject to which it is to be administered. Once the amino acid sequence of each protein is deduced from the DNA sequence, it is possible to synthesize, using standard peptide synthesis techniques and/or recombinant techniques, peptide fragments that are homologous to immunoreactive regions of the protein and to modify these fragments by inclusion, deletion or modification of particular amino acid residues in the derived sequences. Thus, synthesis or purification of an extremely large number of peptides derived from the original protein sequence is possible.

The amino acid sequences of the present polypeptides can contain an immunoreactive portion attached to sequences designed to provide for some additional property, such as solubility. Furthermore, the amino acid sequences can include sequences in which one or more amino acids have been substituted with another amino acid to provide for some additional property, such as to remove/add amino acids capable of disulfide bonding, to increase its biolongevity, alter enzymatic activity, or alter interactions with gastric acidity. In any case, the peptide must posses a bioactive property, such as hemolysin regulation, hemolysis, immunoreactivity, immunogenicity, etc.

The purified polypeptide fragments thus obtained can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter an animal so inoculated with the antigen can be exposed to the bacterium to test the potential vaccine effect of the specific immunogenic fragment. The specificity of a putative immunogenic fragment can be ascertained by testing sera, other fluids or lymphocytes from the inoculated animal for cross reactivity with other closely related bacteria.

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

An antibody which specifically binds an antigenic portion of the protein is also provided for each claimed protein. The antibodies can specifically bind a unique epitope of the antigen or they can also bind epitopes of other organisms. Thus, the antibodies can be used to detect a particular organism or related organisms. The term "specifically bind" means an antibody specifically binding a protein does not cross react substantially with any antigen other than the one specified, in this case, the hemolysin positive regulatory protein or the hemolysin protein, such that the intended antigen can be detected. Antibodies can be made by well-known methods, such as described in Harlow and Lane, *Antibodies; A Laboratory Manual*, Cold Spring Harbor Laboratory, Cold Spring Harbor, N.Y., (1988). Briefly, purified protein, or an antigenic fragment thereof is injected into an animal in an amount and in intervals sufficient to elicit an immune response. Polyclonal antibodies can be purified directly by passing serum collected from the animal through a column to which non-hemolysin regulatory proteins or non-hemolysin proteins prepared from the same expression system have been bound. Monoclonal antibodies can also be produced by obtaining spleen cells from the animal. The cells are then fused with an immortal cell line and screened for antibody secretion. The antibodies can be used to screen DNA clone libraries for cells secreting the antigen. Those positive clones can then be sequenced if desired (see, for example, Kelly et al., *Bio/Technology* 10:163–167, (1992) and Bebbington et al., *Bio/Technology* 10:169–175, (1992)).

The antibody can be bound to a substrate or labeled with a detectable moiety or both bound and labeled. The detectable moieties contemplated with the composition of the present invention, include, for example, fluorescent, enzymatic and radioactive markers.

The present invention additionally provides an immunogenic amount of the protein, i.e., an antigen, in a pharmaceutically acceptable carrier. This composition can include can be the entire antigen, the antigen on an intact avirulent Mycobacterium, *E. coli* or other strain, or an epitope specific to the antigen. The antigen can also be potentially cross-reactive with antibodies to other antigens. The composition can then be used in a method of preventing tuberculosis or other complications of *M. tuberculosis* infection.

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

Hosts of this invention can be in a composition with a pharmaceutically acceptable carrier, particularly if the host is to be administered to a subject. The pharmaceutically acceptable carrier described in the instant invention can comprise saline or other suitable carriers (Arnon, R. (Ed.) *Synthetic Vaccines* I:83–92, CRC Press, Inc., Boca Raton, Fla., 1987). A carrier can be used with this composition of this invention. An adjuvant can also be a part of the carrier of the host, in which case it can be selected by standard criteria based on the antigen used, the mode of administration and the subject (Arnon, R. (Ed.), 1987). Methods of administration can be by oral or sublingual means, or by injection, depending on the particular host used and the subject to whom it is administered.

It can be appreciated from the above that the host containing the herein described nucleic acid can be used as a prophylactic or a therapeutic modality. Thus, the invention provides methods of preventing or treating infection and the associated diseases by administering the host having the described nucleic acid to a subject.

The present invention further provides a method of promoting an immune response in a subject against *Mycobacterium tuberculosis* comprising administering to the subject a host containing a vector which includes an isolated double-stranded nucleic acid comprising the coding sequence set forth in SEQ ID NO:2. The administration of the host can stimulate cell-mediated immunity, as well as humoral immunity, to protect against *M. tuberculosis* infection. The immune response can be detected by standard means known in the art. Administration can be performed according to standard means known in the art for current *M. tuberculosis* vaccines, such as *M. bovis* BCG, including mode of administration and dosages.

Additionally, provided herein is a method of enhancing the immunogenity in a subject of an *M. bovis* BCG vaccine comprising inserting a vector which includes an isolated double-stranded nucleic acid comprising the coding sequence of the sequence set forth in SEQ ID NO:2 into the *M. bovis* BCG vaccine prior to administering the vaccine to the subject. This method can enhance the longevity of effectiveness of standard *M. bovis* BCG vaccines by stimulating cell-mediated immunity. The enhanced vaccine would then be administered as usual for *M. bovis* BCG vaccines, at the known doses.

The invention also provides a method of detecting the presence of a virulent strain of *M. tuberculosis* in a sample comprising identifying the presence of a *M. tuberculosis* nucleic acid sequence in the sample and detecting contact mediated hemolytic activity in the sample. Thus, avirulent and virulent strains of *M. tuberculosis* can be distinguished. Such a "sample" can include cultured isolates obtained directly from a subject. A crude lysate of a culture, or a sputum sample for example, can be utilized to detect the presence of *M. tuberculosis* nucleotide by any several methods known to those of skill in the art (see generally, Sambrook et al.). For example, a nucleic acid specific for *M. tuberculosis* can be detected utilizing a nucleic acid amplification technique, such as polymerase chain reaction or ligase chain reaction. Alternatively, the nucleic acid is detected utilizing direct hybridization or by utilizing a restriction fragment length polymorphism. In addition, PCR primers which hybridize only with nucleic acids specific for *M. tuberculosis* can be utilized. The presence of amplification indicates the presence of the *M. tuberculosis* nucleic acid. In another embodiment a restriction fragment of a DNA sample can be sequenced directly using, for example, Sanger ddNTp sequencing or 7-deaza-2'-deoxyguanosine 5'-triphosphate and Taq polymerase and compared to known unique sequences to detect *M. tuberculosis*. Examples of known *M. tuberculosis* sequences include the IS6110 insertion sequence (Care et al., *Molecular and Cellular Probes*, 5:73–80 (1991), the major polymorphic tandem repeat (MPTR) sequence (Hermans et al., J. Bact.,174:4157–4165 (1992) and the 65K antigen of *M. tuberculosis* (Shinnick, T. M., *J. Bacteriol.*, 169:1080–1088 (1987)).

Samples that contain *M. tuberculosis* DNA can then be analyzed for hemolytic activity by utilizing the hemolysis assay described herein on cell samples. The presence of hemolytic activity in the cell indicates a cell that naturally expresses the hemolysin, i.e., a virulent strain.

The present invention is more particularly described in the following examples which are intended as illustrative only since numerous modifications and variations therein will be apparent to those skilled in the art.

EXAMPLES

Throughout this application, various publications are referenced. The disclosures of these publications in their entireties are hereby incorporated by reference into this application in order to more fully describe the state of the art to which this invention pertains.

Polymerase Chain Reaction

Primers were generated to a 1.6 kbp DNA region in the plasmid pTBLA3 flanking the hpr gene and the reported sequence of the *E. coli* chromosomal region containing the umuD gene (Walker et al., 1985). Amplification of the *E. coli* genomic DNA and the plasmid pTBLA3 was performed using 10 ul of template DNA (20–100 ng) and 90 ul of a reaction mixture consisting of 200 uM (each) deoxynucleotide triphosphates, 1.0 uM (each) primers, 2.5 U Taq polymerase, 10 mM-Tris/HCL (pH 8.3), 50 mM-KCL, 1.5 mM-MgCl$_2$ and 0.01% gelatin as supplied by the Taq polymerase manufacturer (Perkin-Elmer Cetus, Norwalk, Conn.). A three-step cycle of denaturation for 1.45 min at 94° C., annealing for 1.45 min at 55° C., and extension for 3.00 min at 72° C. was performed for 35 cycles on a programmable thermal cycler (Perkin-Elmer Cetus). DNA fragments were sized on a 0.7% TBE agarose gel as described above.

Nucleotide Sequence Analysis

Sequencing was performed using the Prism™ Ready Reaction DyeDeoxy™ Terminator cycle sequencing kit and a 373 DNA sequencing system according to the manufacturer (Applied Biosystems, Inc., Foster City, Calif.). M13 forward and reverse primers were used for initial sequencing of the DNA inserts in the plasmids pTBLA3 and pTBLA3/S2, and internal primers were constructed from these sequence data for overlapping sequence analysis using a DNA synthesizer (model 381A; Applied Biosystems) in the National Center for Infectious Diseases Biotechnology Core Facility. Both strands of the *E. coli* hpr gene and the DNA region containing the umuD gene upstream to this gene were sequenced independently, and sequence data was edited using the Sequence Editor software package (Applied Biosystems). Sequence analysis and data-base searches were performed using the GCG Wisconsin sequence analysis package (version 7.3, Devereux, 1984) and GenBank (includung release 81.0, February 1994).

Hemolytic Activity

*M. tuberculosis* strains H37Rv (TMC #102) and H37Ra (TMC #201), and *M. bovis* BCG were originally obtained from the Trudeau Institute, and stored at −70° C. until use. *E. coli* strain XL1-Blue was purchased from Stratagene Cloning Systems (La Jolla, Calif.) and *E. coli* strain DH5α was purchased from Gibco BRL (Grand Island, N.Y.). Prior to each experiment, mycobacteria strains were grown as static cultures in complete Middlebrook 7H9 broth (Difco) at 37° C. for 4 weeks, and *E. coli* strains were grown as shaken cultures in Luria-Bertani (LB) broth with or without appropriate antibiotics at 37° C. to stationary phase.

Blood agar plates used to screen the hemolytic phenotype in *E. coli* and *M. smegmatis* were prepared by washing citrated whole sheep blood (obtained from the Animal Products Division, CDC) twice with 0.01M phosphate buffered saline (pH 7.2). Washed sheep blood was then added to Trypticase Soy Agar (TSA) at a concentration of 5% with or without the appropriate antibiotics. *E. coli* and *M. smegmatis* transformants were incubated on this medium at 37° C. for 24 h and 4 days, respectively.

Virulent H37Rv (TMC 102) and avirulent H37Ra (TMC 201) strains of *Mycobacterium tuberculosis* were screened for contact-dependent lysis of sheep erythrocytes using a modification of standard erythrocyte lysis assays (20,22). Lysis was monitored by the absorbance of a cell-free supernatant at 540 nm, which measures the release of hemoglobin from erythrocytes. Bacilli were harvested by centrifugation (17,500×g) for 10 min, washed, and resuspended in 0.1% Tween 80/0.01M phosphate buffered saline (PBS) (pH 7.2) at a concentration of ~10$^{12}$ bacteria/ml. Sheep erythrocytes were obtained from whole blood by The Animal Products Division, Centers for Disease Control and Prevention, and were washed and resuspended in 0.1% Tween 80/0.01M PBS (pH 7.2) at a concentration of ~10$^{10}$ cells/ml. For co-sedimentation experiments, equal volumes of the erythrocyte and bacterial suspensions were mixed, centrifuged at 17,500×g for 10 min, and then incubated at 37° C. Mixtures of individual cultures of washed *M. tuberculosis* and *M. bovis* strains with erythrocytes were also incubated at 37° C. without sedimentation. After 3 h, the samples were centrifuged at 17,500×g for 10 min, the supernatants were carefully collected, and their absorbance at 540 nm ($A_{540}$) measured. Mean hemoglobin release was calculated by subtracting the $A_{540}$ of parallel samples containing sheep erythrocytes only that were centrifuged and incubated as described above.

When suspensions of the virulent H37Rv bacilli and erythrocytes were co-sedimented by centrifugation at 17,500×g for 10 min and the pellets incubated at 37° C. for 3 h, the mean hemoglobin release was $A_{540}=0.67\pm0.36$. Hemoglobin release was significantly lower ($A_{540}=0.19\pm0.04$; p=0.026) when the virulent H37Rv bacilli and erythrocytes were mixed and left in suspension without centrifugation. In contrast to the virulent H37Rv, the avirulent H37Ra bacilli produced only an $A_{540}=0.21\pm0.16$ after centrifugation and incubation with sheep erythrocytes, an absorbance not significantly different from the control lysate (p=0.092). The attenuated vaccine strain *M. bovis* BCG produced an $A_{540}=0.06\pm0.03$ after centrifugation and incubation.

Subsequent contact hemolysis experiments using *E. coli* and *E. coli* recombinants were performed as described above with two exceptions. PBS without Tween 80 was used to wash and resuspend bacteria and erythrocytes, and we used ~10$^9$ bacteria/ml and ~10$^{10}$ erythrocytes/ml for each assay with or without sedimentation.

Screening of Cosmid Library for Contact-Dependent Hemolytic Activity

A cosmid library of the *M. tuberculosis* H37Rv strain was constructed using the plasmid pairs pJC98 and pJC100 (24). The plasmids pUC19 and pBluescript II KS- (Stratagene) were used for subcloning the isolates conferring contact-dependent cytolysis in *E. coli* using procedures as described (22).

Overnight cultures of individual transformants of the cosmid library of *M. tuberculosis* H37Rv DNA in *E. coli* K-12 strain XL1-Blue were screened for contact-dependent hemolysis of sheep erythrocytes. A single clone expressing cytolytic activity, designated pHK101, was isolated from a screen of 96 transformants. Only stationary cultures of this recombinant were found to express cytolytic activity. To ensure that the contact-dependent cytolytic activity of this recombinant, pHK101, was due to a gene(s) carried on the cosmid and not an unrelated alteration in the *E. coli* genome, pHK101 DNA was purified and transformed into fresh competent cells of the nonhemolytic *E. coli* strains XL1-Blue and DH5α. Both of these new transformants lysed the erythrocytes, while neither of the naive recipient strains caused any significant lysis.

The contact-dependent cytolytic activity of XL1-Blue (pHK101) cells was compared with that of XL1-Blue cells containing the plasmids pJC98 or pJC100 which were used to construct the cosmid library. Sedimentation of ~10$^9$ XL1-Blue (pHK101) bacteria with erythrocytes produced an $A_{540}=0.24\pm0.028$, while sedimentation of ~10$^9$ XL1-Blue (pJC98), XL1-Blue (pJC100), or XL1-Blue bacteria with sheep erythrocytes produced an $A_{540}<0.02$. XL1-Blue (pHK101) produced significantly less hemoglobin release (p=0.019) when the bacteria were not centrifuged with sheep erythrocytes. Filtrates of stationary phase cultures of XL1-Blue (pHK101) did not produce significant hemoglobin release (p>0.05).

Genetic Analysis

The cosmid pHK101 contains approximately 32 kb of *M. tuberculosis* DNA. XbaI fragments of the pHK101 cosmid were subcloned into the XbaI site of pUC19 and the transformants screened for zones of hemolysis in phosphate buffered saline-washed sheep erythrocytes embedded in Luria-Bertani-top agar. Only recombinants carrying a 6.5 kb XbaI fragment were surrounded by a ring of lysed erythrocytes. Stationary phase cultures of $\sim 10^9$ *E. coli* carrying this plasmid (designated pHK1001) produced a mean hemoglobin release of $A_{540}=0.652\pm0.012$, compared with an $A_{540}$ of $0.241\pm0.029$ from $10^9$ bacteria carrying the cosmid pHK101. The cytolytic activity of XL1-Blue transformed with pHK1001 was also restricted to the stationary phase of growth, and culture filtrates from stationary phase cultures did not induce lysis of sheep erythrocytes. The cytolytic activity was further localized to a 3.2 kb NotI fragment from the plasmid pHK1001 by cloning this fragment into pBluescript II KS⁻. This plasmid was designated pTBLA3. This fragment hybridized to identically sized NotI fragments in genomic DNAs from *M. tuberculosis* H37Rv, *M. tuberculosis* H37Ra, and *M. bovis* BCG. These regions may represent homologs of the regulator gene in these organisms.

Genetic Analysis of Hemolysin Induction by hpr in *E. coli* and *M. smegmatis*

Initial analysis of the gene responsible for this hemolytic phenotype in *E. coli* was performed by subcloning the 1,978 bp Not I/Sal I fragment from the plasmid pTBLA3/S2 (King et al., 1994), and screening subclones for hemolysis on blood agar plates. The plasmid pTBLA3/S2 was digested with a Not I/Sal I double digest and the 1,978 bp fragment was purified from a 1.0% Tris-borate-EDTA (TBE) agarose gel using Geneclean II (Bio 101, LaJolla, Calif.) according to the manufacturers' directions. This DNA fragment was then cleaved into two fragments using a Bgl II digest identified after sequence analysis of this DNA fragment. This generated an 852 bp fragment with Bgl II/Not I sites and a 1,126 bp fragment containing Bgl II sites. These two fragments were purified from a 1% TBE agarose gel as described above, ligated separately into the BamH I or BamH I/Not I sites of pBluescript II$^{ks-}$ and transformed into *E. coli* strain XL1-Blue. All transformants were screened for zones of hemolysis on blood agar plates containing 50 µg/ml ampicillin and incubated at 37° C. for 24 h.

Partial deletion of the umuD gene contained in the 1,978 bp fragment was performed to determine the importance of its role in the induction of hemolysin in *E. coli* and *M. smegmatis*. A 404 bp fragment containing a 151 bp deletion of the umuD gene was cloned out of the plasmid pTBLA3/S2 by digestion with the enzyme HinC II, and purification and religation of the remaining gene sequence to the purified parent vector was performed as described above. The 404 bp fragment containing the 151 bp partially deleted umuD gene was also purified and ligated back to the parent plasmid. Both subclones were screened for zones of hemolysis on blood agar plates as described above. The ability of the reported umuD gene sequence to complement this phenotype in *E. coli* was then tested by cloning the plasmid pSE117 containing the umu operon (Walker, 1984) into *E. coli* XL1-Blue. Transformants containing this plasmid were then tested with the contact-hemolysin assay and for hemolysis on blood agar plates as described above.

The 1,978 bp fragment from the plasmid pTBLA3/S2 was also analyzed for the presence of an independent promoter for the transcription of hpr in *E. coli*. This was done by subcloning the 1,978 bp EcoR I/Sal I fragment from the plasmid pTBLA3/S2 into the EcoR I/Sal I sites of the plasmids pUC18 and pUC19. These clones were then screened for the hemolytic phenotype on blood agar plates containing 50 ug/ml ampicillin, and insert orientations were confirmed by sizing the DNA fragments on a 0.7% TBE agarose gel after digestion of the plasmids with the enzymes Nde I/Cla I. The enzyme Nde I cuts the plasmids pUC19 and pUC18 once and the Cla I enzyme only cuts once within the 1,978 bp insert.

Expression in *Mycobacterium smegmatis*

Evaluation of the induction of a hemolytic phenotype in *M. smegmatis* was performed by cloning the DNA fragments that induced this phenotype in *E. coli* into the electroporatable *M. smegmatis* strain LR222. The 3.2 kbp BamHI fragment from the plasmid pTBLA3 (King et al., 1993) containing hpr was cloned into *E. coli* strain XL1-Blue using the BamHI sites of the *E. coli*/mycobacterial shuttle vector pMV261 (Stover et al., 1991) and this plasmid was designated pMV261/S3. The plasmid pMV261 was also cloned into *E. coli* strain XL1-Blue without insert for a plasmid control. Purified plasmids from *E. coli* were transformed into *M. smegmatis* strain LR222 and the transformants were plated on blood agar plates containing 50 µg/ml kanamycin, incubated at 37° C. for four days, and scored for zones of hemolysis.

Plasmids pMV261/S3 and pMV261 were purified from the hemolytic and nonhemolytic *M. smegmatis* clones, respectively. The DNA insert in the plasmid pMV261/S3 was confirmed by cloning the plasmid back into *E. coli* strain XL1-Blue, purifying the plasmid from hemolytic *E. coli* transformants, and sizing the insert on a 1.0% TBE agarose gel after digestion with the enzyme BamHI. Hemolytic and nonhemolytic *M. smegmatis* and *E. coli* clones on blood agar plates were also tested using the contact-dependent hemolysis assay.

Then it was determined if the putative promoter to hpr was functional in the induction of the hemolytic phenotype in *M. smegmatis* by cloning the 1,978 bp fragment containing hpr into *M. smegmatis* in opposite orientations to the mycobacteria promoter on the plasmid pMV261. The enzyme Sal I was used to isolate the 1,978 bp fragment with Sal I ends from the plasmid pTBLA3 and cloned into *E. coli* XL1-Blue using the Sal I site of the vector pMV261. The plasmids of several hemolytic *E. coli* transformants were screened for the two different Sal I orientations in the vector pMV261 by digestion with enzyme Cla I and sizing the fragments on a 1.0% TBE agarose gel as described above. Both orientations were presumed to induce hemolysin in *E. coli* due to the independently functioning promoter region located upstream from the hpr gene on this fragment. The pMV261 plasmids containing both orientations of the Sal I fragment (designated pMV261/S2 and pMV261/S2°) were purified and then electroporated into *M. smegmatis* strain LR222. *M. smegmatis* transformants were screened for hemolysis on blood agar plates containing kanamycin, and plasmids were confirmed by purification and cloning back into *E. coli* as described above.

Minicell Analysis

The plasmids pMV261, pMV261/S3 and pMV261/S2 were cloned separately into the *E. coli* minicell strain 678–54 (Alder et al., 1967) and hemolytic and nonhemolytic clones confirmed using blood agar plates and the contact-dependent hemolysis assay. Minicells were isolated from these *E. coli* clones using as previously described (Quinn and Tompkins, 1989) after growing these clones to early stationary phase in LB medium containing the 50 ug/ml kanamycin. [$^{35}$S]-methionine labeled proteins were analyzed on a 10% SDS-PAGE along with protein standards. The gels were stained with Coomassie blue, fixed with En$^3$hance solution according to the manufacturer (Dupont, Boston, Mass.), and dried down onto filter paper. Gels were exposed to Kodak AR X-ray film for 24 hours at −70° C.

The *E. coli* subclone containing a 3.2 kbp Not I fragment from the cosmid pHK101 was found to produce clear zones of hemolysis on blood agar plates containing washed sheep erythrocytes, but no zones of hemolysis were produced by this clone on blood agar plates prepared with whole blood. This subclone also produced a contact-dependent hemolysis of sheep erythrocytes similar to that of the *E. coli* clone containing pHK101. When this 3.2 kbp fragment was cloned into *E. coli* using the vector pMV261 (plasmid designated pMV261/S3) and then purified and cloned from a hemolytic *E. coli* transformant into the *M. smegmatis* strain LR222, this DNA fragment was also found to induce zones of hemolysis in mycobacterial transformants after growth on blood agar plates incubated for 4 days. *E. coli* and *M. smegmatis* transformants containing the vector pMV261 were nonhemolytic after 4 days culture on blood agar plates and *M. smegmatis* transformants remained negative after 14 days incubation. Although both *E. coli* and *M. smegmatis* transformants containing the vector pMV261/S3 were hemolytic on blood agar plates, only the *E. coli* transformants produced contact-dependent hemolysis of washed sheep erythrocytes.

Size analysis of the DNA insert in the plasmid pMV261/S3 was performed on the plasmid after replication in *E. coli* and *M. smegmatis*. These studies demonstrated that a deletion within the 3.2 kbp BamH I fragment occurred when this plasmid was cloned into *M. smegmatis*. The supercoiled plasmid isolated directly from *M. smegmatis* was approximately 6.0 kbp and the BamH I fragment isolated from this plasmid after transformation and replication in *E. coli* was 1.5 kbp.

Partial sequence analysis and data base search of the 3.2 kbp fragment in the plasmid pTBLA3 demonstrated that this fragment contained homologous regions of the umuD and umuC genes which matched 100% to the DNA sequence on the *E. coli* chromosomal region containing the umu operon reported by Kitagawa et al., 1985 and Perry et al., 1985. Subcloning of this DNA insert was performed to determine which gene located on this insert encoded the hemolytic phenotype in *E. coli* and *M. smegmatis*. A 1,978 bp Sal I/Not I fragment subcloned from the plasmid pTBLA3 into the vector pMV261 was found to induce hemolysis of *E. coli* and *M. smegmatis* transformants. Partial sequence analysis of this 1,978 bp insert in the plasmid pTBLA3/S2 demonstrated that in addition to the partial sequence of umu operon, this fragment also contained an unreported 852 bp DNA sequence upstream from the homologous Bgl II site of the reported DNA sequence for the chromosomal region containing umuD.

Subclone analysis of this 1,978 bp insert indicated that the umuD gene was not responsible for induction of the hemolytic phenotype in *E. coli* or *M. smegmatis*. A Bgl II fragment subcloned from the 1,978 bp fragment containing the intact umuD gene and its promoter cloned into the vector pBluescript II$^{ks-}$ was unable to confer a hemolytic phenotype to *E. coli* transformants. *E. coli* transformants carrying the Bgl II/Not I fragment from this insert were also nonhemolytic. Partial deletion of the umuD gene from the plasmid pTBLA3/S2 had no effect on the hemolytic phenotypes of *E. coli* transformants carrying this plasmid. *E. coli* clones containing the deleted portion of umuD and partial sequence of umuC were nonhemolytic. In addition, the same *E. coli* strains transformed with the plasmid pSE117 which contains the cloned chromosomal regions of the *E. coli* umu operon were nonhemolytic on blood agar plates or by the contact-dependent hemolysin assay.

DNA amplification of the *E. coli* strain XL1-Blue chromosome using primers constructed to a flanking region of the umuD gene and the unreported DNA sequence located upstream to umuD on the 1,978 bp fragment resulted in the amplification of an identically sized fragment of 1.6 kbp from the genomic DNA of *E. coli* and the plasmid pTBLA3 when sized on a 0.7% TBE agarose gel.

Opposite orientations of the 1,978 bp fragment in relation to the LacZ promoter in the vectors pUC18 and pUC19 had no effect on the hemolytic phenotypes of *E. coli* transformants containing these plasmids indicating the presence of an independent promoter that was functional in *E. coli*. A Sal I fragment containing this insert was ligated into opposite orientations with respect to the hsp60 promoter in the Sal I site of the vector pMV261 and these two plasmids, pMV261/S2 and pMV26152°, were cloned into *E. coli* strain XL1-Blue. This placed the transcription of the gene on this DNA insert in opposite orientations with respect to the hsp60 promoter in pMV261 and was done to determine if the independent promoter was functional in *M. smegmatis*. *E. coli* transformants containing pMV261/S2 and pMV261/S2° were equally hemolytic on blood agar plates. In contrast, only *M. smegmatis* transformants containing the plasmid pMV261/S2° were hemolytic. These results demonstrate that the independent promoter for the gene that induced hemolysin in *E. coli* was not functional in *M. smegmatis*. Orientation of this gene under control of the hsp60 promoter in pMV261 did induce the hemolytic phenotype in *M. smegmatis* demonstrating that transcription of the hpr gene on the 1,978 bp fragment that induced hemolysin was opposite to the homologous DNA sequence containing the umuD gene. Hemolytic clones of *M. smegmatis* containing pMV261/S2° were also found to form large aggregates of cells during cultivation in 7H9 and TSA broth compared to nonhemolytic clones containing pMV261.

Complete sequence analysis of the 1,978 bp fragment confirmed the presence of a second open reading frame believed to encode hpr on the opposite strand and in the opposite orientation to the homologous DNA sequence containing umuD. This hpr sequence is set forth in SEQ ID NO:2 (1021 bp). The orientation of the sense strand containing this open reading frame was in agreement with the expression of a hemolytic phenotype induced by this gene in *M. smegmatis* using the vector pMV261 as shown above. No other continuous open reading frames of greater than 50 amino acids were found on this DNA fragment. The DNA sequence contains an overall G+C composition of 40.8% which is atypical for *E. coli* DNA sequences (Marmur and Doty, 1962). There is a 5/6 match of DNA sequence located 17 bp upstream to the putative start codon of hpr with the −10 consensus sequence for *E. coli* promoters (TATAAT), and a 4/6 match of sequence to the −35 consensus sequence (TTGACA) located 46 bp upstream to this codon. There is also a possible ribosome binding site that has a 4/8 match to the *E. coli* consensus sequence (AGGAAAGG) 9 bp upstream from the putative ATG codon.

If the putative ATG codon at position 99 of the DNA sequence for this open reading frame is assumed to be the initiator codon and a stop codon is located in frame to this open reading frame after the Not I site on the cloning vector, then this open reading frame encodes a protein of 309 amino acids ending with an alanine. The predicted molecular weight for this protein based on the DNA sequence is approximately 34,000 daltons. It was unusual that this open reading frame did not contain a stop codon, but the predicted molecular weight of the protein encoded by hpr using the vector stop codon sequence matched the actual protein expressed in *E. coli* minicells containing this gene. Hemolytic clones of *E. coli* minicells containing pMV261/S2° expressed an approximately 34,000 dalton protein whereas nohemolytic *E coli* minicells containing pMV261 did not produce this protein. This suggests that the stop codon located on the vector sequence and in frame to the hpr open reading frame was functional for termination of the hpr gene and that this gene was required for induction of the hemolytic phenotype in these *E coli* clones.

The DNA sequence containing the putative open reading frame for hpr was searched for homology at the DNA and amino acid level. The DNA sequence contained a 62.0% homology to the Chlamydial hctA gene over a 129 bp region. This gene has been described to encode a lysine-rich histone-like DNA binding protein involved in nucleoid condensation (Hackstadt et al., 1991). The hpr gene also had a 55.9% homology to the *Actinobacillus pleuropneumoniae* apxI operon with a 102 bp region containing the open reading frame for the apxIA structural gene for hemolysin. In addition, there was a 62.0% homology over a 100 bp region and a 53.3% homology over a 225 bp region for the *Lactococcus lactis* LacR gene and the *M. gallisepticum* ATP operon respectively.

The ability to lyse membranes in other bacteria suggests that cytolysins play roles in processes such as invasion or entry into eukaryotic cells, intracellular multiplication, cell-to-cell spread, or escape from membrane-bound vacuoles or cells (Mims, C. A. et al., *The Pathogenesis of Infectious Disease*, Academic Press, Inc., San Diego, Calif. (1990)). The genomic locus for contact-dependent cytolysis in the virulent *M. tuberculosis* strain H37Rv is homologous to genomic regions in the attenuated strains *M. tuberculosis* H37Ra and *M. bovis* BCG, and thus, these strains may be attenuated due to their lack of or lowered expression of this cytolytic activity. The hybridization and amplification data also indicates that there is an *M. tuberculosis* homolog to the *E. coli* umuCD operon.

Another possible role for this cytolytic activity may be in the release of mycobacteria from heavily laden macrophages. Such a role would be compatible with the observation that only *E. coli* recombinants from stationary-phase cultures express this cytolytic activity. The possible roles of cytolysins in pathogenesis are not limited simply to the lysis of membranes. Even in the absence of lysis, bacterial cytolysins can exert profound pleiotropic effects on eukaryotic cells (for a review see Welch, R. A. et al., *Infect. Immun.*, 43:156–160 (1991)). For example, energy metabolism may be disrupted (Bhakdi, S. et al., *J. Clin. Invest.*, 85:1746–1753 (1990)) or the ability to respond to exogenous signals may be impaired (Welch, R. A. et al., *The Molecular Biology of Microbial Pathogenicity*, Academic Press, Inc., New York (1986).

Therefore, the gene for the regulator of hemolysin, e.g., as listed in SEQ ID NO:2, can be the basis of a vaccine against tuberculosis. The gene can be inserted into an avirulent vaccine strain such as *M. bovis* BCG, by means known and standard in the art. This modified virus can then be administered as a vaccine, following methods and dosages currently used to administer *M. bovis* BCG as a vaccine. The inventive vaccine can infect macrophages, as do the prior *M. bovis* BCG vaccines; however, the inventive vaccine, with its hemolysin regulator gene, can have the added ability to escape phagosomes into the cytoplasm, for presentation of antigens and resultant cell-mediated immunity.

Although the present invention has been described with reference to specific details of certain embodiments thereof, it is not intended that such details should be regarded as limitations upon the scope of the invention except as and to the extent that they are included in the accompanying claims.

REFERENCES

1. Armstrong, J. A. and P. D. Hart. 1971. Response of cultural macrophages to *Mycobacterium tuberculosis*, with observations on fusion of lysosomes and phagosomes. *J. Exp. Med.*, 134:713–740.
2. Barnes, P. F., A. B. Bloch, P. T. Davidson, and D. E. Snider, Jr. 1991. Tuberculosis in patients with human immunodeficiency virus infection. *N. Engl. J. Med.*, 324:1644–1650.
3. Beecher, D. J., and J. D. MacMillan. 1990. A novel hemolysin from *Bacillus cereus*. *Infect. Immun.* 58:2220–2227.
4. Berche, P. A., J. L. Gaillard, and P. J. Sansonetti. 1987. Intracellular growth of Listeria monocytogenes as a prerequisite for in vivo induction of T cell-mediated immunity. *J. Immunol.* 138:2266–2271.
5. Bernheimer, A. W. 1988. Assay of hemolytic toxins. *Methods Enzymol.* 165:213–217.
6. Bhakdi, S., M. Muhly, S. Korom, and G. Schmidt. 1990. Effects of *Escherichia coli* hemolysin on human monocytes. *J. Clin. Invest.* 85:1746–1753.
7. Bielecki, J., P. Youngman, P. Connelly, and D. A. Portnoy. 1990. *Bacillus subtilis* expressing a haemolysin gene from Listeria monocytogenes can grow in mammalian cells. *Nature* (London) 345:175–176.
8. Brownlie, R. M., J. G. Coote, R. Parton, J. E. Schultz, A. Rogel, and E. Hanski. 1988. Cloning of the adenylate cyclase genetic determinant of *B. pertussis* and its expression in *E. coli* and *B. pertussis*. *Mol. Pathog.* 4:335–344.
9. Chaisson, R. R., G. F. Schecter, C. P. Theuer, G. W. Rutherford, D. F. Echenberg, and P. C. Hopewell. 1987. Tuberculosis in patients with the acquired immunodeficiency syndrome: clinical features, response to therapy, and survival. *Am. Rev. Respir. Dis.* 136:570–574.
10. Cluff, C. W., M. Garcia, and H. K. Ziegler. 1990. Intracellular hemolysin-producing Listeria monocytogenes strains inhibit macrophage-mediated antigen processing. *Infect. Immun.* 58:3601–3612.
11. Cluff, C. W., and H. K. Ziegler. 1987. Inhibition of macrophage-mediated antigen presentation by hemolysin-producing Listeria monocytogenes. *J. Immunol.*, 139:3808–3812.
12. Cossart, P., M. F. Vicente, J. Mengaud, F. Baquero, J. C. Perez-Diaz, and P. Berche. 1989. Listeriolysin O is essential for virulence of Listeria monocytogenes: Direct evidence obtained by gene complementation. *Infect. Immun.* 57:3629–3636.
13. Crowle, A. J. 1988. The *tubercle bacillus*-human macrophage relationship studied in vitro, p. 99–135. In M. Bendinelli and H. Friedman,(ed.), *Mycobacterium tuberculosis*. Interactions with the immune system. *Plenum Publishing Corp.*, New York.
14. Crowle, A. J., R. Dahl, E. Ross, and M. H. May. 1991. Evidence that vesicles containing living, virulent *Mycobacterium tuberculosis* or *Mycobacterium avium* in cultured human macrophages are not acidic. *Infect. Immun.* 59:1823–1831.

15. Gaillard, J. L., P. Berch, J. Mounier, S. Richard, and P. Sansonetti. 1987. In vitro model of penetration and intracellular growth of Listeria monocytogenes in the human enterocyte-like cell line Caco-2. *Infect. Immun.*, 55:2822–2829.
16. Gordon, A. H., P. D Hart, M. R. Young. 1980. Ammonia inhibits phagosome-lysosome fusion in macrophages. Nature (London) 286:79–80.
17. Hart, P. D., J. A. Armstrong, C. A. Brown, and P. Draper. 1972. Ultrastructural study of the behavior of macrophages infected with *Mycobacterium tuberculosis*. Infect. Immun. 5:803–807.
18. Kuhn, M., S. Kathariou, and W. Goebel. 1988. Hemolysin supports survival but not entry of the intracellular bacterium Listeria monocytogenes. *Infect. Immun.* 56:79–82.
19. Leake, E. S., Q. N. Myrvik, and M. J. Wright. 1984. Phagosomal membranes of *Mycobacterium bovis* BCG-immune alveolar macrophages are resistant to disruption by *Mycobacterium tuberculosis* H37Rv. *Infect. Immun.* 45:443–446.
20. Lucus, S. B. 1989. Mycobacteria and the tissues of man, p.108–176. In C. Ratledge, J. Stanford, and J. M. Grange (ed.), *The Biology of the Mycobacteria*, Vol. 3. Academic Press, Inc., Ltd., London.
21. Mackeness, G. B. 1952. The action of drugs on intracellular *tubercle bacilli*. *J. Pathol. Bacteriol.* 64:429–446.
22. Maniatis, T., E. F. Fritsch, and J. Sambrook. 1982. *Molecular cloning: A Laboratory Manual*, Cold Spring Harbor Laboratory, Cold Spring Harbor, N.Y.
23. Mims, C. A. 1990. *The Pathogenesis of Infectious Disease*, Academic Press, Inc., San Diego.
24. Mundayoor, S., et al. Unpublished data.
25. Murray, C. J. L., K. Styblo, and A. Rouillon. 1990. Tuberculosis in developing countries: burden, intervention and cost. *Bull. Int. Union Tuberc.* 65:6–24.
26. Myrvik, Q. N., E. S. Leake, and M. J. Wright. 1984. Disruption of phagosomal membranes of normal alveolar macrophages by the H37Rv strain of *Mycobacterium tuberculosis*: a correlate of virulence. *Am. Rev. Respir. Dis.*, 129:322–328.
27. Portnoy, D. A., P. S. Jacks, and D. J. Hinrichs. 1988. Role of hemolysin for the intracellular growth of Listeria monocytogenes. *J. Exp. Med.*, 167:1459–1471.
28. Rennie, R. P., and J. P. Arbuthnott. 1974. Partial characterization of *Escherichia coli* haemolysin. *J. Med. Microbiol.* 7:179–188.
29. Rogel, A., R. Meller, and E. J. Hanski. 1991. Adenulate cyclase toxin from *Bordetella pertussis*. *J. Biol. Chem.* 266:3154–3161.
30. Sansonetti, P. J. 1991. Genetic and molecular basis of cell invasion by *Shigella spp*. *Rev. Infect. Dis.* 13(Suppl.4):285–292.
31. Sansonetti, P. J., A. Ryter, P. Clerc, A. T. Maurelli, and J. Mounier. 1986. Multiplication of *Shigella flexneri* with HeLa cells: lysis of the phagocytic vacuole and plasmid-mediated contact hemolysis. *Infect. Immun.* 51:461–469.
32. Schlesinger, L. S., C. G. Bellinger-Kawahara, N. R. Payne, M. A. Horwitz. 1990. Phagocytosis of *Mycobacterium tuberculosis* is mediated by human monocyte complement receptors and complement component C3. *J. Immunol.* 144:2771–2780.
33. Weiss, A. A., L. Hewlett, G. A. Myers, and S. Falkow. 1983. Tn5-induced mutations affecting virulence factors of *Bordetella pertussis*. *Infect. Immun.* 42:33–41.
34. Welch, R. A. 1991. Pore-forming cytolysins of gram-negative bacteria. *Mol. Microbiol.* 5:521–529.
35. Welch, R. A., and S. Falkow. 1984. Characterization of *Escherichia coli* hemolysins conferring quantitative differences in virulence. *Infect. Immun.* 43:156–160.
36. Welch, R. A., T. Felmlee, F. Pellett, and D. E. Chenoweth. 1986. The *Escherichia coli* haemolysin: Its gene organization and interaction with neutophil receptors, p. 431–438. In D. L. Lark, S. Normark, B. E. Uhlin, and H. Wolf-Watz, (ed.), *Protein-Carbohydrate Interactions in Biological Systems: The Molecular Biology of Microbial Pathogenicity*, Academic Press, Inc., New York.
37. Zychlinsky, A., M. C. Prevost, and P. J. Sansonetti. 1992. *Shigella flexneri* induces apoptosis in infected macrophages. *Nature* (London) 358:167–169.
38. Jacobs, W. R. Jr., G. V. Kalpana, J. D. Cirillo, L. Pascopella, S. B. Snapper, R. A Udani, W. Jones, R. g. Barletta, and B. R. Bloom, Genetic systems for Mycobacteria, *Methods in Enzymology*, 204:537–555.
39. Kitagawa, Y. E., Akaboshi, H. Shinagawa, T. Horii, H. Ogawa, and T. Kato. 1985. Structural analysis of the umu operon required for inducible mutagenesis in *Escherichia coli*. *Proc. Natl. Acad. Sci. USA* 82:4336–4340.
40. Perry, K. L., S. J. Elledge, B. B. Mitchell, L. Marsh, and G. C. Walker. 1985. umuDC and mucAB operons whose products are required for UV light- and chemical-induced mutagenesis: UmuD, MucA, and LexA proteins share homology. *Proc. Natl. Acad. Sci. USA*, 82:4331–4335.
41. Devereux, J., P. Haeberli, and O. Smithies. 1984. A comprehensive set of sequence analysis programs for the VAX. *Nucleic Acids Res.* 12:387–395.
42. Hackstadt, T., W. Baehr, Y. Yuan. 1991. *Proc. Natl. Acad. Sci. U.S.A.* 88:3937
43. Wilson. K. 1990. Preparation of genomic DNA from bacteria. In *Current Protocols in Molecular Biology*, vol. 1, pp. 2.4.1–2.4.2. Edified by F. M. Ausubel, R. Brent, R. E. Kinston, D. D. Moore, I. G. Seidman, J. A. Smith, and K. Struhl. New York, Wiley Interscience.
44. Yakrus, M. A., M. W. Reeves, and S. B. Hunter. 1992. Characterization of isolates of *Mycobacterium avium* serotypes 4 and 8 from patients with AIDS by multilocus enzyme electrophoresis. *J. Clin. Microbiol.* 30:1474–1478.

What is claimed is:

1. The isolated double-stranded nucleic acid set forth in SEQ ID NO:2.

2. The nucleic acid of claim 1 in a vector.

3. An isolated nucleic acid comprising nucleotides 99–1020 of the nucleic acid of claim 1.

4. An isolated nucleic acid comprising SEQ ID NO:2.

5. The nucleic acid of claim 4 operably linked to a reporter gene.

6. The nucleic acid of claim 5 in a vector.

7. The vector of claim 6 in a host suitable for expression of the nucleic acid.

8. An isolated nucleic acid encoding a purified protein comprising the polypeptide set forth in SEQ ID NO:3.

9. A vector comprising the nucleic acid of claim 8.

10. The vector of claim 9 in a host suitable for expression of the nucleic acid.

11. The vector of claim 10, wherein the host is M. bovis BCG.

12. The vector of claim 10, wherein the host is Mycobacterium smegmatis.

13. A method of promoting an immune response in a subject against Mycobacterium tuberculosis comprising administering to the subject the host of claim 11.

14. A method of promoting an immune response in a subject against Mycobacterium tuberculosis comprising administering to the subject the host of claim 12.

15. A method of enhancing the immunogenicity of an M. bovis BCG vaccine in a subject: comprising inserting the vector of claim 9 into the M. bovis BCG vaccine prior to administering the vaccine to the subject.

* * * * *